US00PP13563P2

(12) United States Plant Patent
Trees

(10) Patent No.: US PP13,563 P2
(45) Date of Patent: Feb. 18, 2003

(54) GERANIUM PLANT NAMED 'BALCOLCORK'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/099,390

(22) Filed: Mar. 15, 2002

(51) Int. Cl.[7] ..... A01H 5/00
(52) U.S. Cl. ..... Plt./332
(58) Field of Search ..... Plt./332

*Primary Examiner*—Kent L. Bell
(74) *Attorney, Agent, or Firm*—C. A. Whealy

(57) ABSTRACT

A new and distinct cultivar of Geranium plant named 'Balcolcork', characterized by its cascading and mounded growth habit; freely basal branching habit; dark green-colored leaves with darker zonation pattern; and light red-colored double flowers.

1 Drawing Sheet

BOTANICAL CLASSIFICATION/CULTIVAR DESIGNATION

*Pelargonium peltatum* cultivar 'Balcolcork'.

BACKGROUND OF THE INVENTION

The present invention relates to a new and distinct cultivar of Geranium plant, botanically known as *Pelargonium peltatum*, and hereinafter referred to by the name 'Balcolcork'.

The new Geranium is a product of a planned breeding program conducted by the Inventor in Arroyo Grande, Calif. The objective of the breeding program was to develop new freely flowering Geraniums with attractive flower and foliage colors.

The new Geranium originated from a cross-pollination made by the Inventor of a proprietary *Pelargonium peltatum* selection identified as code number BFP-2175, not patented, as the female, or seed, parent with a proprietary *Pelargonium peltatum* selection identified as code number BFP-2022, not patented, as the male, or pollen, parent. The cultivar 'Balcolcork' was discovered and selected by the Inventor as a flowering plant within the progeny from this cross-pollination in a controlled environment in Arroyo Grande, Calif., in 1999.

Asexual reproduction of the new cultivar by terminal cuttings taken at Arroyo Grande, Calif., since June, 2000, has shown that the unique features of this new Geranium are stable and reproduced true to type in successive generations of asexual reproduction.

SUMMARY OF THE INVENTION

The following traits have been repeatedly observed and are determined to be the unique characteristics of 'Balcolcork'. These characteristics in combination distinguish 'Balcolcork' as a new and distinct cultivar:

1. Cascading and mounded growth habit.
2. Freely basal branching habit.
3. Dark green-colored leaves with darker zonation pattern.
4. Light red-colored double flowers.

Plants of the new Geranium differ from plants of the parent selections primarily in flower color.

The new Geranium can be compared to the cultivar 'Flair', not patented. However, in side-by-side comparisons conducted in Arroyo Grande, Calif., plants of the new Geranium differed from plants of the cultivar 'Flair' in the following characteristics:

1. Plants of the new Geranium had shorter lateral branches with shorter internodes than plants of the cultivar 'Flair'.
2. Leaves of plants of the new Geranium had a distinct zonation pattern whereas leaves of plants of the cultivar 'Flair' did not have a distinct zonation pattern.
3. Plants of the new Geranium had shorter peduncles and pedicels than plants of the cultivar 'Flair'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Geranium.

The photograph at the top of the sheet comprises a side perspective view of a typical flowering plant of 'Balcolcork'.

The photograph at the bottom of the sheet comprises a close-up view of typical flowers of 'Balcolcork'.

DETAILED BOTANICAL DESCRIPTION

The cultivar 'Balcolcork' has not been observed under all possible environmental conditions. The phenotype may vary somewhat with variations in environment such as temperature and light intensity, without, however, any variance in genotype. The aforementioned photographs and following observations and measurements describe plants grown 10-cm pots in Arroyo Grande, Calif., under commercial practice in a polycarbonate-covered greenhouse with day temperatures about 20 to 22° C., night temperatures about 18 to 20° C. and light levels about 2,500 to 3,000 foot-candles. Plants used for the photographs and description were about 8 to 10 weeks from planting rooted cuttings. In the following description, color references are made to The Royal Horticultural Society Colour Chart, 1995 Edition, except where general terms of ordinary dictionary significance are used.

Botanical classification:

*Pelargonium peltatum* cultivar 'Balcolcork'.

Parentage:

*Female parent.*—Proprietary *Pelargonium peltatum* selection BFP-2175, not patented.

*Male parent.*—Proprietary *Pelargonium peltatum* selection BFP-2022, not patented.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Cascading and mounded growth habit. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about four lateral branches at the base. Pinching, that is, removal of terminal apices, is typically not required.

*Plant height* (*to top of foliage*).—About 13 cm.

*Plant width.*—About 28.3 cm.

*Lateral branches.*—Length: About 16.8 cm. Internode length: About 1.3 cm. Texture: Smooth, glabrous. Color: Darker than 144A.

*Foliage description.*—Leaves simple, generally symmetrical, abundant, opposite. Quantity of leaves per lateral branch: About 20. Length: About 3.2 cm. Width: About 6 cm. Shape: Reniform. Apex: Broadly acute. Base: Cordate. Margin: Palmatifid. Venation pattern: Palmate. Texture, upper and lower surfaces: Densely pubescent. Color: Young foliage, upper surface: Slightly more yellow than 138A. Young foliage, lower surface: 146A. Fully expanded foliage, upper surface: Between 131A and 147A; zonation pattern between 147A and 200B and located towards the center of leaf; venation, 144B. Fully expanded foliage, lower surface: 164A; venation, 146C. Petiole: Length: About 3.6 cm. Diameter: About 2 mm. Color: 146A.

Flower description:

*Flower arrangement and type.*—Light red-colored flowers arranged in hemispherical umbels arising from apical leaf axils. Umbels displayed above the foliage. At full flowering, usually about ten open umbels and developing umbels per plant. Flowers double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About seven. Diameter: About 8.1 cm. Height: About 4.1 cm. Flower diameter: About 4.5 cm. Flower height (depth): About 1.9 cm.

*Flower buds.*—Length: About 1.5 cm. Diameter: About 9 mm. Shape: Ovoid. Color: 40B.

*Petals/petaloids.*—Quantity: About twelve petals and about three petaloids per flower. Petaloids variable in size and shape. Arrangement: Imbricate. Petal length: Upper petals: About 2.9 cm. Lower petals: About 2.5 cm. Petal width: Upper petals: About 1.9 cm. Lower petals: About 1.7 cm. Petal shape: Obovate. Petal/petaloid apex: Obtuse. Petal/petaloid base: Attenuate. Petal/petaloid margin: Enitre. Petal/petaloid texture, upper and lower surfaces: Velvety; glabrous. Petal/petaloid color: When opening and fully opened, upper surface: Upper petals/petaloids: Closest to 52A; basal veins, 61A; basal spot, 45A. Lower petals/petaloids: Closest to 52A. When opening and fully opened, lower surface: Upper petals/petaloids: Closest to 48C; venation, 61B. Lower petals/petaloids: Closest to 48C.

*Sepals.*—Quantity: About five, not imbricate. Length: About 1.2 cm. Width: About 3 mm. Shape: Ensiform. Apex: Narrowly acute. Margin: Entire. Texture, upper and lower surfaces: Pilose. Color, upper and lower surfaces: 146A.

*Peduncle* (*umbel stem*).—Length: About 8.8 cm. Angle: Erect. Strength: Strong. Texture: Dense pubescence. Color: Slightly darker than 144A.

*Pedicel* (*individual flower stem*).—Length: About 2.1 cm. Angle: Erect. Strength: Strong. Texture: Dense pubescence. Color: 144A; occasionally overlain with between 176A and 178B.

*Reproductive organs.*—Androecium: Anther quantity: About eleven. Anther length: About 2 mm. Anther color: Closest to 83B. Pollen amount: Moderate. Pollen color: Closest to 169B. Gynoecium: Pistil quantity: One. Pistil length: About 1.4 cm. Stigma shape: Five-parted, star-shaped. Stigma color: Closest to 53B. Style length: About 4 mm. Style color: Closest to 2D.

*Seed/fruit.*—Seed and fruit development has not been observed.

Disease/pest resistance: Resistance to pathogens and pests common to Pelargonium has not been observed.

It is claimed:

1. A new and distinct cultivar of Geranium plant named 'Balcolcork', as herein illustrated and described.

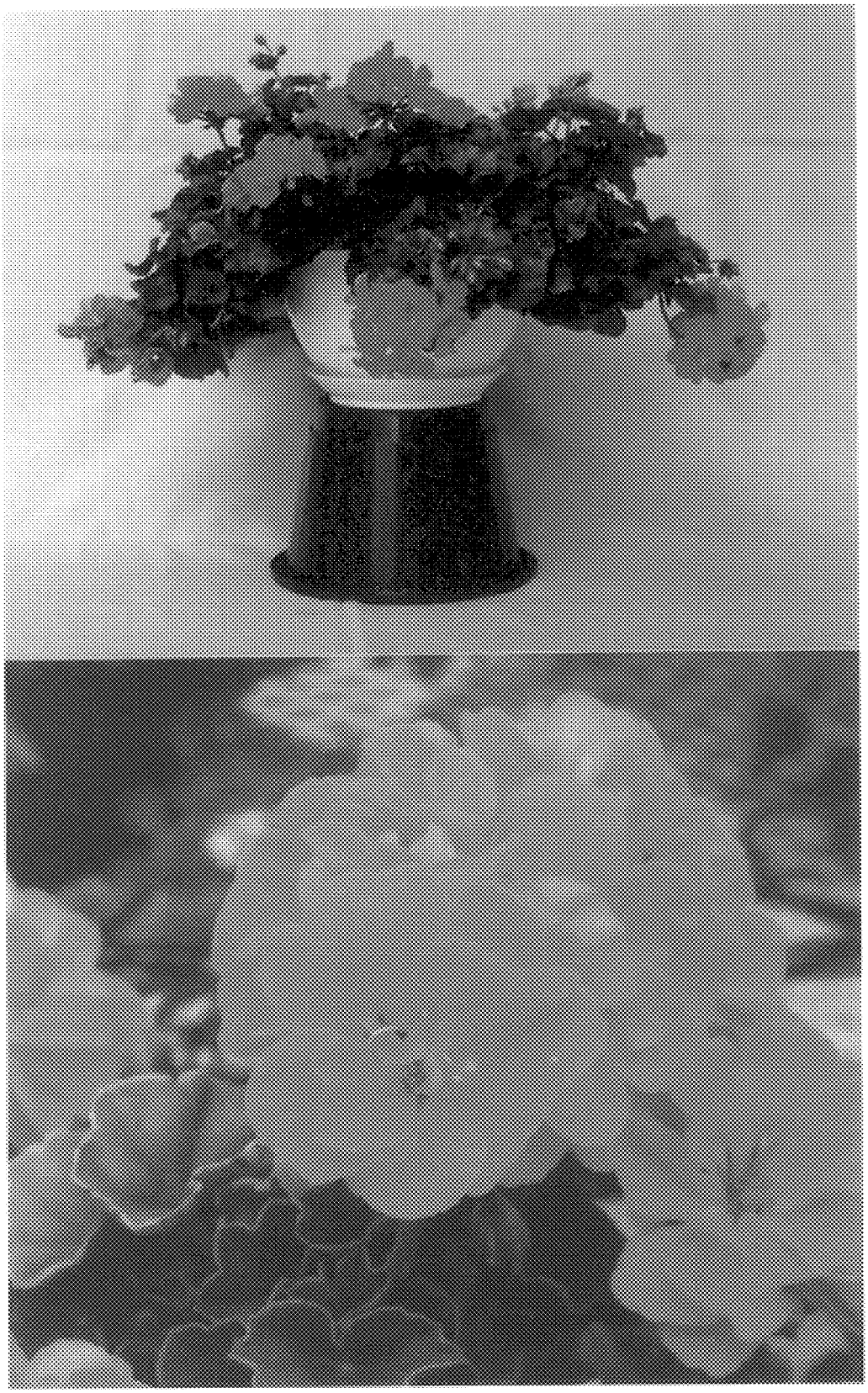

* * * * *